United States Patent [19]

O'Brien et al.

[11] Patent Number: 5,017,556
[45] Date of Patent: May 21, 1991

[54] TREATMENT OF BLEEDING DISORDERS USING LIPID-FREE TISSUE FACTOR PROTEIN

[75] Inventors: Donogh P. O'Brien, Bromley, England; Gordon A. Vehar, San Carlos, Calif.

[73] Assignee: Genentech, Inc., South San Francisco, Calif.

[21] Appl. No.: 320,876

[22] Filed: Mar. 8, 1989

Related U.S. Application Data

[63] Continuation of Ser. No. 110,255, Oct. 20, 1987, abandoned, which is a continuation-in-part of Ser. No. 926,977, Nov. 4, 1986, abandoned.

[51] Int. Cl.$^5$ .................... A61K 37/02; A61K 37/04; C07K 15/16
[52] U.S. Cl. .......................................... 514/2; 514/8; 514/21; 530/381; 530/380; 530/382; 530/383; 530/384; 530/395; 530/359; 530/422; 530/424; 530/829; 530/830
[58] Field of Search ................ 514/2, 8, 21; 424/101, 424/45; 530/381

[56] References Cited

U.S. PATENT DOCUMENTS

| | | | |
|---|---|---|---|
| 2,516,216 | 7/1950 | Kazal et al. | 530/381 |
| 2,847,350 | 8/1958 | Singher | 530/381 |
| 3,980,432 | 9/1976 | Trobisch et al. | 424/95 |
| 4,416,812 | 11/1983 | Becker et al. | 530/381 |

OTHER PUBLICATIONS

Rao et al., Anal. Biochem. 165:365-370 (1987).
Bom et al., Thromb. Res. 42:635-643 (1986).
Guha et al., Proc. Natl. Acad. Sci. U.S.A. 83:299-302 (1986).
Carson et al., Science 229:991-993 (1985).
Carson, FEBS Letters 132(1):37-40 (1981).
Osterud, Scand. J. Haematol., 32:337-345 (1984).
Giercksky et al., Scand. J. Haematol., 16:300-310 (1976).
Lewis et al., J. Lab & Clin. Med. 60(2):261-273 (1962).
Gollub et al., Thromb. Diath. Haemorh. 7:470-479 (1962).
Osterud, Biochem. Biophys. Res. Comm. 88(1):59-67 (1979).
Carson et al., Blood 66(1):152-156 (1985).
Gonmori et al., Biblio. Haematol., 49:23-39 (1983).
Ewan et al., J. Immunol. 136(7):2408-2415 (1986).
Morrissey et al., 59th Sci. Sessions (Nov. 19, 1986) American Heart Assoc. (Oral Presentation, Notes Attached).
Bach et al., 59th Sci. Sessions (Nov. 19, 1986) American Heart Assoc. (Oral Presentation, Notes Attached).
The U.S. Pharmacopeia (Rev. 21), Section 1211: pp. 1347-1493, Jan. 1, 1985.
The U.S. Pharmacopeia (Rev. 21), Section 1151: pp. 1338-1339, Jan. 1, 1985.
Bach et al., J. Biol. Chem., 256(16), 8324-31, (1981).
Broze et al., J. Biol. Chem., 260(20), 10917-20, (1985).
Bjorklind et al., Biochem. J., 165, 89-96, (1977).
Freyssinet et al., Thromb. Haemostasis, 55(1), 112-18, (1986).
Tanaka et al., Thromb. Res., 40(6), 745-56, (Dec. 1985).
Osterud, Scand. J. Haemotol., 32, 337-45, (1984).
Kurosawa et al., Thromb. Res., 33, 595-606, (1984).
Carlson et al., Thromb Haemostasis, 48(3), 315-19, (1982).

*Primary Examiner*—Esther L. Kepplinger
*Assistant Examiner*—Jeff Kushan
*Attorney, Agent, or Firm*—Max D. Hensley; Daryl B. Winter

[57] ABSTRACT

A method and therapeutic composition for the treatment of bleeding disorders, for example those characterized by a tendency toward hemorrhage or a hypercoagulative state, by the administration of tissue factor protein or antagonists thereof.

15 Claims, 3 Drawing Sheets

Fig. 3.

TREATMENT OF BLEEDING DISORDERS USING LIPID-FREE TISSUE FACTOR PROTEIN

This is a continuation of U.S. Ser. No. 07/110,255, filed Oct. 20, 1987, now abandoned, which is a continuation-in-part of U.S. Ser. No. 06/926,977, filed Nov. 4, 1986, now abandoned.

BACKGROUND OF THE INVENTION

This invention relates to the treatment of bleeding disorders. In particular, this invention relates to the use of tissue factor protein to effect haemostasis in certain clinical conditions and particularly in animals lacking certain coagulation proteins. Factor VIII and factor IX deficiencies are two examples.

Bleeding is one of the most serious and significant manifestations of disease. It may occur from a local site or may be generalized. Bleeding associated with a local lesion may be superimposed on either a normal or a defective haemostatic mechanism. Normal haemostasis comprises mechanisms operative immediately following an injury and those acting over a longer period. Primary haemostasis consists principally of two components: vasoconstriction and platelet plug formation. The maintenance mechanism consists of the fibrin clot produced by the coagulation system. Platelet plug formation is especially important in capillary haemostasis, while vasoconstriction and fibrin clot formation is more important in larger vessel haemostasis. In the microcirculation haemostasis consists of asoconstriction and platelet plug formation. Platelet plug formation may be divided into several stages: adhesion of platelets to subendothelial surfaces exposed by trauma; platelet activation release reaction; platelet aggregation, which results in the sequestration of additional platelets at the site, and the binding of fibrinogen and the coagulation proteins to the platelet surface which includes thrombin formation; and, fusion which is the coalescence of fibrin and fused platelets to form a stable haemostatic plug.

Blood coagulation performs two functions; the production of thrombin which induces platelet aggregation and the formation of fibrin which renders the platelet plug stable. A number of discrete proenzymes and procofactors, referred to as "coagulation factors", participate in the coagulation process. The process consists of several stages and ends with fibrin formation. Fibrinogen is converted to fibrin by the action of thrombin. Thrombin is formed by the proteolytic cleavage of a proenzyme. prothrombin. This proteolysis is effected by activated factor X (referred to as factor $X_a$) which binds to the surface of activated platelets and in the presence of Va and ionic calcium cleaves prothrombin.

Figures 1, 2:
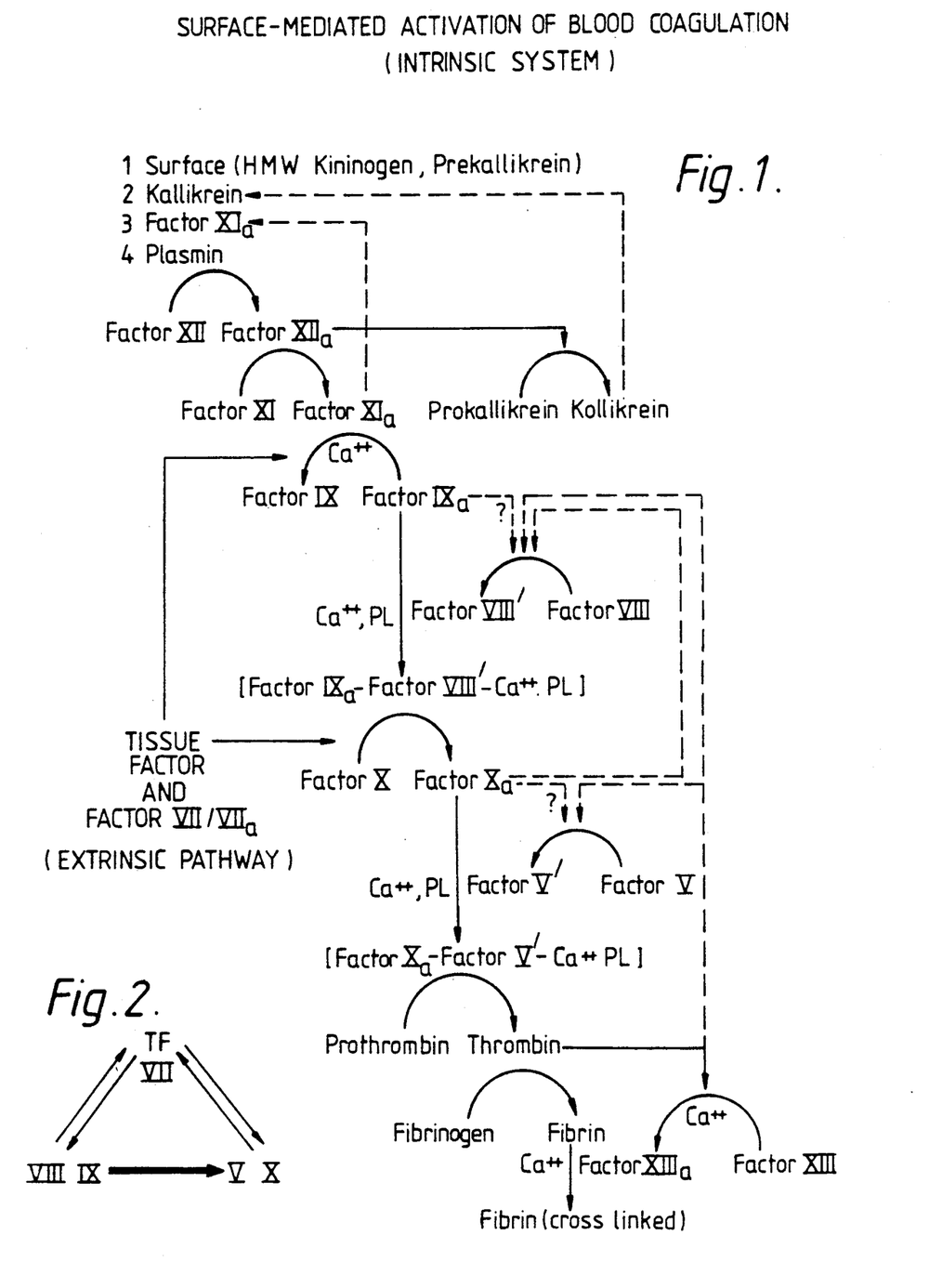
FIG. 1. Diagram showing activation of blood coagulation via intrinsic pathway.
FIG. 2. Diagram showing amplification of coagulation signal via extrinsic pathway.

Activation of factor X may occur by either of two separate pathways, the extrinsic or the intrinsic (FIG. 1). The intrinsic cascade consists of a series of reactions wherein a protein precursor is cleaved to form an active protease. At each step, the newly formed protease will catalyze the activation of the precursor protease at the subsequent step of the cascade. A deficiency of any of the proteins in the pathway blocks the activation process at that step, thereby preventing clot formation and typically gives rise to a tendency to hemorrhage. Deficiencies of factor VIII or factor IX, for example, cause the severe bleeding syndromes haemophilia A and B, respectively In the extrinsic pathway of blood coagulation, tissue factor, also referred to as tissue thromboplastin, is released from damaged cells and activates factor X in the presence of factor VII and calcium. Although activation of factor X was originally believed to be the only reaction catalyzed by tissue factor and factor VII, it is now known that an amplification loop exists between factor X, factor VII, and factor IX (Osterud, B., and S. I. Rapaport, Proc. Natl. Acad. Sci. USA 74:5260-5264, 1977; Zur, M. et al., Blood 52: 198, 1978). Each of the serine proteases in this scheme is capable of converting by proteolysis the other two into the activated form, thereby amplifying the signal at this stage in the coagulation process (FIG. 2). It is now believed that the extrinsic pathway may in fact be the major physiological pathway of normal blood coagulation (Haemostasis 13: 150-155 1983). Since tissue factor is not normally found in the blood, the system does not continuously clot; the trigger for coagulation would therefore be the release of tissue factor from damaged tissue.

Tissue factor is an integral membrane glycoprotein which. as discussed above, can trigger blood coagulation via the extrinsic pathway. Bach, R. et al., J. Biol. Chem. 256(16), 8324-8331 (1981). Tissue factor consists of a protein component (previously referred to as tissue factor apoprotein-III) and a phospholipid. Osterud, B. and Rapaport, S. I., PNAS 74, 5260-5264 (1977). The complex has been found on the membranes of monocytes and different cells of the blood vessel wall. Osterud, B., Scand J. Haematol. 32, 337-345 (1984). Tissue factor from various organs and species has been reported to have a relative molecular mass of 42,000 to 53.000. Human tissue thromboplastin has been described as consisting of a tissue factor protein inserted into phospholipid bilayer in an optimal ratio of tissue factor protein:phospholipid of approximately 1:80 Lyberg, T. and Prydz. H., Nouv. Rev Fr. Hematol 25(5), 291-293 (1983). Purification of tissue factor has been reported from various tissues such as: human brain (Guha, A. et al. PNAS 83, 299-302 [1986]and Broze, G. H. et al., J. Biol. Chem. 260[20], 10917-10920 [1985]); bovine brain (Bach, R. et al., J. Biol. Chem. 256, 8324-8331 [1981]); human placenta (Bom, V. J. J. et al., Thrombosis Res. 42:635-643 [1986]; and. Andoh, K. et al., Thrombosis Res. 43:275-286 [1986]); ovine brain (Carlsen, E. et al., Thromb. Haemostas. 48[3], 315-319 [1982]); and, lung (Glas, P. and Astrup, T., Am J. Physiol. 219, 1140-1146 [1970]. It has been shown that bovine and human tissue thromboplastin are identical in size and function. See for example Broze, G. H. et al., J. Biol. Chem. 260(20), 10917-10920 (1985) It is widely accepted that while there are differences in structure of tissue factor protein between species there are no functional differences as measured by in vitro coagulation assays. Guha et al. supra. Furthermore, tissue factor isolated from various tissues of an animal, e.g. dog brain, lung, arteries and vein was similar in certain respects such as, extinction coefficient, content of nitrogen and phosphorus and optimum phospholipid to lipid ratio but differed slightly in molecular size, amino acid content, reactivity with antibody and plasma half life. Gonmori. H. and Takeda, Y., J. Physiol. 229(3), 618-626 (1975). All of the tissue factors from the various dog organs showed clotting activity in the presence of lipid. Id. It is widely accepted that in order to demonstrate biological activity, tissue factor must be associated with phospholipids. Pitlick. F. A., and Nemerson. Y., Biochemistry 9, 5105-5111 (1970) and Bach, R. et al. supra. at 8324. It has been shown that the removal of the phospholipid component of tissue factor, for example by use of a phospholipase, results in a loss of its biological activity. Nemerson, Y., J.C.I. 47, 72-80 (1968). Relipidation can restore in vitro tissue factor activity. Pitlick, F. A and Nemerson, Y. Biochemistry 9, 5105-5113 (1970) and Freyssinet, J. M. et al., Thrombosis and Haemostasis 55, 112-118 [1986].

Infusion of tissue factor has long been believed to compromise normal haemostasis. In 1834 the French physiologist de Blainville first established that tissue factor contributed directly to blood coagulation. de Blainville H. Gazette Medicale Paris, Series 2, 524 (1834). de Blainville also observed that intravenous infusion of a brain tissue suspension caused immediate death which he observed was correlated with a hypercoagulative state giving rise to extensively disseminated blood clots found on autopsy. It is now well accepted that intravenous infusion of tissue thromboplastin induces intravascular coagulation and may cause death in various animals. (Dogs: Lewis, J. and Szeto I. F., J. Lab. Clin. Med. 60, 261-273 (1962); rabbits: Fedder. G. et al., Thromb. Diath. Haemorrh. 27, 365-376 (1972); rats: Giercksky, K. E. et al., Scand. J. Haematol. 17 305-311 (1976); and, sheep: Carlsen, E. et al., Thromb Haemostas. 48, 315-319 [1982]).

In addition to intravascular coagulation or a hypercoagulative state resulting from the exogenous administration of tissue factor, it has been suggested that the intravascular release of tissue thromboplastin may initiate disseminated intravascular coagulation (DIC). Prentice, C. R., Clin. Haematol. 14(2), 413-442 (1985). DIC may arise in various conditions such as shock, septicaemia, cardiac arrest, extensive trauma, bites of poisonous snakes, acute liver disease, major surgery, burns, septic abortion, heat stroke, disseminated malignancy, pancreatic and ovarian carcinoma, promyelocytic leukemia, myocardial infarction, neoplasms, systemic lupus erythematosus, renal disease and eclampsia. Present treatment of DIC includes transfusion of blood and fresh frozen plasma; infusion of heparin; and removal of formed thrombi. The foregoing clinical syndromes suggest that endogenous release of tissue factor can result in severe clinical complications. Andoh, K. et al., Thromb. Res 43, 275-286 (1986). Efforts were made to overcome the thrombotic effect of tissue thromboplastin using the enzyme thromboplastinase. Gollub, S. et al., Thromb. Diath. Haemorh. 7, 470-479 (1962). Thromboplastinase is a phospholipase and would presumably cleave the phospholipid portion of tissue factor. Id.

Congenital disorders of coagulation characteristically involve a single coagulation protein. Haemophilia is a bleeding disorder due to inherited deficiency of a coagulation factor. e.g. the procoagulant activity of factor VIII. The basis of therpay of bleeding episodes is transfusion of material containing the missing coagulation protein, e.g. infusion of factor VIII procoagulant activity which temporarily corrects the speicific defect of haemophilia A.

Von Willebrand's disease is another bleeding disorder characterized by a prolonged bleeding time in association with an abnormality or deficiency in the von Willerand protein. Treatment is by infusion of normal plasma or by a composition rich in von Willebrand protein. Congenital deficiencies of each of the other coagulation factors occur and may be associated with a haemorrhagic tendency. The present therapies for the deficiencies are: factor IX deficiency is treated using concentrates containing factor IX: infusions of plasma are given for a factor XI deficiency; and plasma infusion is given for a factor XIII deficiency.

Acquired coagulation disorders arise in individuals without previous history of bleeding as a result of a disease process. Inhibitors to blood coagulation factors may occur in multitransfused individuals. Acquired coagulation factor deficiencies with unknown etiology also give rise to haemostatic problems. DIC describes a profound breakdown of the haemostatis mechanism.

An object of the present invention is to provide a coagulation inducing therapeutic composition for various chronic bleeding disorders, characterized by a tendency toward hemorrhage, both inherited and acquired Examples of such chronic bleeding disorders are deficiencies of factors VIII. IX, or XI. Examples of acquired disorders include: acquired inhibitors to blood coagulation factors e g, factor VIII, von Willebrand factor, factors IX, V, XI, XII and XIII; haemostatic disorder as a consequence of liver disease which includes decreased synthesis of coagulation factors and DIC; bleeding tendency associated with acute and chronic renal disease which includes coagulation factor deficiencies and DIC; haemostasis after trauma or surgery; patients with disseminated malignancy which manifests in DIC with increases in factors VIII, von Willebrand factor and fibrinogen; and haemostasis during cardiopulmonary surgery and massive blood transfusion. Another object of this invention is to provide a method of treatment of such chronic bleeding disorders.

A further object of this invention is to provide a coagulation inducing therapeutic composition for acute bleeding problems in normal patients and in those with chronic bleeding disorders. Another object of this invention is to provide a method of treatment for such acute bleeding problems.

Yet another object of this invention is to provide an anticoagulant therapeutic, that is an antagonist to tissue factor protein, to neutralize the thrombotic effects of endogenous release of tissue thromboplastin which may result in a hypercoagulative state. Particularly, such an anticoagulant, that is an antagonist to tissue factor protein, would neutralize the hypercoagulant effects of endogenously released tissue thromboplastin by inactivating tissue factor protein. Such a tissue factor protein antagonist can be an antibody or other protein that specifically inactivates the protein component.

SUMMARY OF THE INVENTION

This invention is based in part on the novel and unexpected observation that infusion of tissue factor protein into rabbits lacking coagulation factors not only corrected haemostatic deficiency but did not induce disseminated intravascular coagulation or result in other adverse side effects. Tissue factor protein is the protein portion of tissue factor lacking the naturally occurring phospholipid, which was previously referred to as tissue factor apoprotein III and previously believed to be inactive. Tissue factor protein was for the first time found to correct the bleeding diathesis, i.e. a tendency toward hemorrhage, associated with factor VIII deficiency in vivo. Furthermore, infusion of tissue factor protein would be expected to be ineffective in light of the papers which describe tissue factor as having an absolute requirement for phospholipid. The efficacy and lack of toxicity observed is in contrast to the results one would have expected from the work of de Blainville and subsequent researchers over the past one hundred and fifty-two years.

Accordingly, in one aspect the invention is directed to administration of a pharmaceutical composition comprising tissue factor protein as a coagulant in patients with bleeding disorders. In another aspect the invention is directed to a method of treatment of chronic bleeding disorders. Yet another aspect is a method of treatment of acute bleeding incidents in patients having chronic bleeding disorders A further aspect of this invention is directed to an anticoagulant to neutralize the coagulant effects of endogenously released tissue thromboplastin by inactivating tissue factor protein.

DETAILED DESCRIPTION

As used herein, "tissue factor protein" refers to a protein capable of correcting various bleeding disorders, particularly those associated with deficiencies in coagulation factors. Tissue factor protein is distinct from tissue factor or tissue thromboplastin in that it lacks the naturally occurring lipid portion of the molecule. Tissue factor protein also includes tissue factor protein associated with phospholipid which lipid is distinct from the naturally occurring lipid associated with tissue thromboplastin and which displays coagulation-inducing capability without the concomitant toxicity observed with the lipidated protein. Infusion of tissue factor protein, as defined herein, does not result in disseminated intravascular coagulation. The capacity of tissue factor protein to correct various bleeding disorders is readily determined using various in vivo bleeding models e.g. initiation of coagulation in hemophilic dogs using cuticle bleeding time determination (Giles, A R. et al., Blood 60:727-730 [1982]).

The term "tissue factor protein antagonists" as used herein refers to substances which may function in two ways. First, tissue factor protein antagonists will bind to tissue factor protein with sufficient affinity and specificity to neutralize tissue factor protein such that it cannot bind to factor VII or $VII_a$ nor effect the proteolysis of factors IX or X when in complex with factor VII or $VII_a$. Alternatively, tissue factor protein antagonists will inactivate tissue factor protein or the tissue factor/factor $VII_a$ complex by cleavage, e.g. a specific protease. Antagonists are useful, either alone or together, in the therapy of various coagulation disorders as evidenced by altered plasma fibrinogen levels as described herein e.g. DIC occurring during severe infections and septicemias, after surgery or trauma, instead of or in combination with other anticoagulants such as heparin.

An example of an antagonist which will neutralize tissue factor protein is a neutralizing antibody to tissue factor protein. Tissue factor protein neutralizing antibodies are readily raised in animals such as rabbits or mice by immunization with tissue factor protein in Freund's adjuvant followed by boosters as required. Immunized mice are particularly useful for providing sources of B cells for the manufacture of hybridomas, which in turn are cultured to produce large quantities of inexpensive anti-tissue factor protein monoclonal antibodies. Such tissue factor protein monoclonal antibodies have been prepared by Carson, S. D. et al., Blood 66(1), 152-156 (1985).

Tissue factor is released from damaged cells and activates factors IX and X in the presence of factor VII or $VII_a$ and calcium. (See FIG. 2) The activation of factor X by the extrinsic pathway of coagulation has an absolute requirement for tissue factor. Silverberg, S. A., et al., J. Biol. Chem. 252, 8481-8488 (1977). Until the discovery of this invention, it was thought that the lipid component of tissue factor was essential for optimal tissue factor activity in the catalysis of factor X or factor IX by factor VII or $VII_a$. This invention encompasses the treatment of various acute and chronic bleeding disorders by bypassing those deficiencies through the administration of tissue factor protein. More particularly this invention is applicable to those bleeding disorders arising in animals deficient in various coagulation factors.

Tissue thromboplastin or tissue factor consists of a glycoprotein component (previously referred to as tissue factor apoprotein III) which has been purified to apparent homogeneity (Bjorklid, E. et al., Biochem. Biophys. Res. Commun. 55, 969-976 [1973]) and a phospholipid fraction. Numerous reports have described the purification of tissue factor from many types of tissue such as brain, lung and placenta. Sheep, cow, rabbit, dog and human have been a source of tissue factor. The first step in the chemical purification has been to dissociate tissue factor from its native lipid using, for example, extraction with organic solvents. Examples of such organic solvents include pyridine. heptane-butanol mixture or ethanol. Tissue factor protein has been purified by chemical means. Examples of such chemical means are: treatment with detergents, such as deoxycholate or Triton X-100; gel filtration and preparative polyacrylamide-gel electrophoresis in the presence of sodium dodecyl sulphate; concanavalin A bound to a Sepharose column; and, affinity columns using antibodies to the tissue factor protein or selective adsorption to factor VII. Included within the scope of tissue factor protein is tissue factor protein from recombinant or synthetic sources. Also included are dimers of tissue factor protein and tissue factor protein variants having amino acid substitutions and/or deletions and/or additions. organic and inorganic salts and covalently modified derivatives of tissue factor protein. Tissue factor protein produced by recombinant means may include a naturally occurring pro-form as well as a prepro-form of tissue factor protein.

For use in this invention tissue factor protein or tissue factor protein antagonists may be formulated into an injectable preparation. Parenteral formulations are suitable for use in the invention, preferably for intravenous administration. These formulations contain therapeutically effective amounts of tissue factor protein, are either sterile liquid solutions, liquid suspensions or lyophilized versions and optionally contain stabilizers or excipients. Typically. lyophilized compositions are reconstituted with suitable diluents, e.g. sterile water for injection. sterile saline and the like where the biological activity is sufficient to induce haemostatic coagulation as observed in a rabbit infusion study.

Alternatively, for use in this invention tissue factor protein can be formulated into a preparation for absorption through the gastrointestinal tract. Such a preparation is suitable for use in the invention for oral administration. Such oral preparations contain therapeutically effective amounts of tissue factor protein, a lipophilic vehicle and a gastrointestinal tract absorption enhancing agent. Suitable lipophilic vehicles include mineral oil, triglycerides, esterified glycols, polyglycols with hydrophobic alkyl side chains, and sterols. Examples of an absorption enhancer include hydroxyaryl or hydroxyaralkyl acids or their salts, esters or amides. Other compounds with similar properties include salicylic acid derivatives, amines of 1,3 dicarbonyl compounds and enamino acids, and their salts, amides and esters.

Tissue factor protein may be administered by injection intravascularly or by oral administration at a dosage sufficient to correct a bleeding disorder, for example, replacement therapy in the face of a factor VIII deficiency. Tissue factor protein may be administered at a dosage sufficient to correct an acute bleeding incident in the face of a coagulation factor deficiency. Therapeutic dosage of tissue factor protein is in the range of about from 10 U/kg to 300 U/kg. A preferred therapeutic dosage of tissue factor protein is in the range of about 50 U/kg to 250 U/kg. A most preferred therapeutic dosage of tissue factor protein is in the range of about 75 U/kg to 200 U/kg. In the absence of an international standard of tissue factor activity we have established a tissue factor standard. A unit of tissue factor activity is that amount of tissue factor protein in 10 $\mu$l of tissue thromboplastin (commercially available from Sigma, St. Louis. Mo.) as measured by the chromogenic assay. See description of chromogenic assay below. The dose will be dependent upon the relative activity of the particular species of tissue factor protein, e.g., human tissue factor protein as compared to bovine tissue factor protein. The relative activities can be determined using the chromogenic assay. If, for example, human tissue factor protein is less active by one-half in an in vivo hemophilic dog model than the bovine tissue factor protein, then the therapeutic dosage range using human tissue factor protein would be increased by a factor of two. The dose will also be dependent upon various therapeutic variables including the animal species to be treated, the route of administration, the properties of the tissue factor protein employed. e.g. its activity and biological half life, the concentration of tissue factor protein in the formulation, the patient's plasma volume, the clinical status of the patient e.g. the particular bleeding disorder, and such other parameters as would be considered by the ordinarily skilled physician.

Tissue factor protein antagonist may be administered by injection intravascularly at a dosage sufficient to correct a bleeding disorder, e.g DIC. Antagonists may be administered at a dosage sufficient to correct such a bleeding disorder. The dose will be dependent on various therapeutic variables known to the ordinarily skilled artisan.

Tissue factor protein also is suitably formulated into a topical preparation for local therapy for minor bleeding occurring from an accessible site in conjunction with a cold application and gentle pressure. Such a preparation for local therapy includes a therapeutically effective concentration of tissue factor protein in a dermatological vehicle. The amount of tissue factor protein to be administered and the tissue factor protein concentration in the topical formulation, will depend on the vehicle selected, the clinical condition, the species of tissue factor protein used and the stability of tissue factor protein in the formulation.

The tissue factor protein or antagonist of this invention preferably is formulated and administered as a sterile solution although it is within the scope of this invention to utilize lyophilized tissue factor preparations. Sterile solutions are prepared by sterile filtration of tissue factor protein or by other methods known per se in the art. The solutions are then lyophilized or filled into pharmaceutical dosage containers. The pH of the solution should be in the range of pH 3.0 to 9.5, preferably pH 5.0 to 7.5. The tissue factor protein should be in a solution having a suitable pharmaceutically acceptable buffer such as phosphate, tris (hydroxymethyl) aminomethane-HCl or citrate and the like. Buffer concentrations should be in the range of 1 to 100 mM. The solution of tissue factor protein may also contain a salt, such as sodium chloride or potassium chloride in concentration of 50 to 750 mM. The compositions of this invention optionally include an effective amount of a stabilizing agent as required such as an albumin, a globulin, a gelatin, mono or polysaccharide, amino acid or sugar. A stabilizing amount of detergent such as non-ionic detergents (PRG or block copolymers), sodium deoxycholate, Triton X-100 or sodium dodecyl sulfate (SDS) may be added.

Tissue factor protein or antagonist preferably is placed into a container having a sterile access port, for example, an intravenous solution bag or vial having a stopper piercable by a hypodermic injection needle.

Systemic administration of tissue factor protein may be made daily or several times a week in the case of replacement therapy for a coagulation factor deficiency. Administration is typically by intravenous injection Administration may also be intranasal or by other nonparenteral routes. Tissue factor protein may also be administered via microspheres, liposomes or other microparticulate delivery systems placed in certain tissues including blood.

EXAMPLE 1

General Materials and Methods

Mature bovine brains were obtained from Pel-Freeze, Rogers. Ar., and stored at $-20°$. Triton X-100 and $\alpha$-D-methylglucoside were from Calbiochem, San Diego, Calif. Concanavalin A-Sepharose resin (referred to as Con A Sepharose in Table 1) was from Pharmacia and Ultrogel AcA 44 from LKB, Gaithersburg, MD. All chemicals and reagents for preparative and analytical sodium dodecyl sulfate polyacrylamide gel electrophoresis (SDS-PAGE) were obtained from Bio-Rad Laboratories, Richmond, Calif. Factor $IX_a$/Factor X reagent and S2222/I2581 were obtained from Helena Laboratories (Kabi Coatest kit, Helena Laboratories, Beaumont, Calif., Catalogue No. 5293). YM 10 ultrafiltration membranes were from Amicon. Factor VII was purified from bovine plasma. (Broze, G. and Majerus, P., J. Biol. Chem. 255(4): 1242–1247 [1980]). Factor VIII deficient and normal pooled citrated plasma were from George King Biomedicals, Overland Park, Kans. Crude phosphotidylcholine (lecithin granules from soya bean) were obtained from Sigma, St. Louis, Mo. All other chemicals were of reagent grade or better.

ACETONE DELIPIDATION OF BOVINE BRAINS

Two mature bovine brains were thawed at room temperature and rinsed free of clotted blood with distilled water. The tissue was then homogenized into ice cold acetone to a volume of 10 ml acetone per gram wet weight of bovine brain using an Ultra-Turrex tissue homogenizer. The homogenate was extracted at 4° C. for 30 min. and then filtered through Whatman No. 1 filter paper on an evacuated flask. The tissue slurry was resuspended in the original volume of ice cold acetone, extracted and filtered for six times The final filter cake was dried under a stream of nitrogen and stored at $-20°$ C.

Triton X-100 Solubilization of Tissue Factor

Acetone brain powders (145 g) were homogenized in 0.05M Tris/0.1M NaCl, pH 7.5 (TBS) to a final volume of 20 ml buffer/g acetone brain powder. The homogenate was extracted at 4° C. for 1 hr. and subsequently centrifuged at 10,000 x g for 1 hr. at 4° C. The supernatant was discarded and the pellet re-homogenized into three (3) liters TBS/0.1% Triton X-100. The material was extracted and centrifuged as before. The pellet thus obtained was then homogenized into three (3) liters TBS/2% Triton X-100 to solubilize tissue factor. The homogenate was extracted for 16 hrs. at 4° C. and then centrifuged as before.

Concanavalin A-Sepharose Affinity Column

The supernatant from the 2% Triton X-100 extraction was made 1 mM in $CaCl_2$ and $MgCl_2$ and batch adsorbed with 100 ml Concanavalin-A Sepharose resin for 16 hrs at 4° C. Following adsorption, the Sepharose resin was poured into a $3 \times 20$ cm column and washed with 500 ml TBS 0.05% Triton X-100 at a flow rate of 2 ml/min. Absorbance was monitored at 280 nM. When no further protein washed from the column, the Sepharose was eluted isocratically with a buffer comprising 100 mg/ml $\alpha$-D methylglucoside in TBS/0.05% Triton X-100. Ten milliliter fractions were collected at a flow rate of 2 ml/min. Fractions were relipidated and assayed for tissue factor activity. Tissue factor protein was eluted in approximately four (4) column volumes of eluant. The eluate was concentrated in an Amicon concentration cell using a YM 10 ultrafiltration membrane.

Gel Permeation Chromatography

Ten milliliters of concentrated Concanavalin-A Sepharose eluate were dialyzed against TBS 0.1% Triton X-100, pH 7.4, 1 L volume with 4 changes buffer. After dialysis for 8 hours the material was applied to a $120 \times 1.5$ cm column of AcA 44 Ultrogel pre-equilibrated with TBS 0.1% Triton X-100. The column was developed isocratically at a flow rate of 6 ml/hr. One milliliter fractions were collected. Fractions were relipidated and assayed for tissue factor activity. Peak fractions were pooled to a final volume of 20 ml. This material was stored at $-20°$ C. prior to use.

Purification of Tissue Factor Protein

Tissue factor protein was partially purified from bovine brain by a combination of acetone delipidation, Triton X-100 extraction, lectin affinity chromatography, and gel permeation chromatography. The highly purified tissue factor protein was 12,000 fold purified from brain powders (Table 1). A sensitive chromogenic assay for tissue factor protein was utilized to monitor purification steps. Following detergent extraction of acetone brain powders, the tissue factor protein activity could not be detected in the assay unless tissue factor protein was relipidated. The material which was infused into the rabbits had no cofactor activity prior to relipidation in either the one stage coagulation assay or the two stage chromogenic assay described below (Table 2). This confirmed the well known phospholipid dependence of tissue factor. See Nemerson, Y., supra. Human placental tissue factor was isolated using known methods, for example, see Guha, A. et al. supra. Human placental tissue factor protein was compared to bovine tissue factor protein. As shown in Table 5. both human placental tissue factor and bovine tissue factor have a lipid requirement for activity in an in vitro chromogenic assay. As discussed above, human placental and bovine tissue factors are similar in structure. Thus, human placental tissue factor would be expected to function similarly to bovine tissue factor if infused into rabbits.

Assay for Tissue Factor Protein

1. Chromogenic tissue factor assay.

All samples extracted from bovine brain by non-ionic detergent were relipidated prior to assay. As discussed above tissue factor has an absolute requirement for phospholipid to exhibit activity in in vitro assay systems (Pitlick and Nemeson, Supra). Lecithin granules were homogenized in Tris 0.05M, 0.1M NaCl pH7.4 (TBS) containing 0.25% sodium deoxycholate to a concentration of 1 mg/ml. This solution (PC/DOC) was used to relipidate tissue factor as follows. Tissue factor protein was diluted into TBS containing 0.1% bovine serum albumin (TBSA).

Fifty microliters were placed in a $12 \times 75$ mm polystyrene test tube and 50 $\mu$l PC/DOC solution was added. Three hundred and fifty (350) microliters TBSA were then added along with 25 $\mu$l 100 mM $CdCl_2$. This relipidation mixture was allowed to incubate at 37° C. for 30 min.

For the chromogenic assay, relipidated tissue factor protein samples were diluted in TBSA. Ten microliters were placed in a test tube with 50 $\mu$l of the factor $IX_a$/-factor X reagent and 2 $\mu$l of a solution of purified factor VII, 30 units/ml. The tubes were warmed to 37° C. and 100 $\mu$l 25 mM $CaCl_2$ were added. Samples were incubated for 5 min. at 37° C. prior to the addition of 50 $\mu$l chromogenic substrate S2222 containing the synthetic thrombin inhibitor I2581. The reaction was allowed to proceed for 10 min. and was stopped by the addition of 100 $\mu$l 50% glacial acetic acid solution. Absorbance was detected at 405 nM. A standard curve was constructed using rabbit brain thromboplastin (commercially available from Sigma, St. Louis, Mo., catalogue #T0263) arbitrarily assigning this reagent as having 100 tissue factor units/ml. Dilutions were made from 1:10 to 1:1000. Absorbance was plotted on the abscissa on semilog graph paper with dilution of standard plotted on the ordinate.

2. One stage assay for tissue factor activity.

100 $\mu$l haemophilic plasma were added to 10 $\mu$l of relipidated or lipid free tissue factor or TBSA as control in a siliconized glass tube to prevent non-specific activation through the contact phase of coagulation. The reactants were warmed to 37° C. and 100 $\mu$l 25 mM $CaCl_2$ were added and clot formation timed. Hvatum, Y. and Prydz, H., Thromb. Diath. Haemorrh. 21, 217-222 (1969).

EXAMPLE 2

Efficacy and Lack of Toxicity of Tissue Factor Protein in a Rabbit Model

Arterial and venous cannulas were inserted into the ears of two 1.8 kg New Zealand white rabbits. 0.8 ml arterial blood was withdrawn from each animal and anticoagulated with 0.2 ml 0.13M trisodium citrate. Both animals were then infused with 600 μl protein-A purified, human, anti-human factor VIII antibody, 1700 Bethesda U/ml, through the venous cannula. Thirty minutes after the infusion, arterial cannulas were flushed with 1 ml saline and 1 ml of blood was withdrawn and discarded. 0.8 ml of blood was then anticoagulated for assay as described above. Three hundred microliters TBS/0.1% Triton X-100 was then infused into the first rabbit as a control while the second rabbit received 300 μl of tissue factor protein. On relipidation, this would represent a dose of 233 tissue factor units per kilogram (U/kg). Sixty minutes after the infusion of the antibody, blood was withdrawn from both rabbits for assay and the arterial cannulas were removed. Blood was collected and flow and duration of blood flow recorded.

Rabbit factor VIII cross-reacted with human anti-human factor VIII antibodies in in vitro assay systems. These antibodies were then used to anticoagulate rabbits thus allowing the demonstration of tissue factor protein's factor VIII by-passing activity in vivo. Thirty minutes after the infusion of anti-factor VIII antibodies, no factor VIII was detected in the plasma by chromogenic factor VIII assay (Table 3). The control rabbit received an infusion of buffer (300 μl) containing 0.1% Triton X-100 thirty minutes before the removal of the arterial vein cannula. This resulted in profuse bleeding which took eleven min, to cease (Table 3). The animal receiving tissue factor protein (test #2, at Table 3) bled only slightly after the same treatment and this flow stopped after 38 seconds demonstrating that tissue factor protein by-passes factor VIII activity in vivo. The animals receiving tissue factor protein had no observed thrombi as had been reported in the literature and discussed above.

The toxicity of the tissue factor protein preparation was tested in six rabbits that were infused with 250 units of tissue factor protein per kilogram. After three days, no adverse effects were observed (Table 4). It should be noted that this is the dose used in Table 3 wherein the bleeding defect was corrected. Two of the rabbits were then infused with a second dose of 250 U/kg, one received twice this dose, and one rabbit received 5 times the dose. These animals, as well as two that did not receive a second injection, were monitored for an additional two days. All animals appeared normal after a total of 120 hours of observation, demonstrating that the material is well tolerated and not toxic. Similar preparations of human tissue factor protein would therefore be expected to be well tolerated when infused into patients (Table 4) and be able to correct bleeding disorders (Table 3).

EXAMPLE 3

Efficacy and Lack of Toxicity of Tissue Factor Protein in a Canine Hemophilia Model Tissue factor protein is infused into hemophilic dogs using the procedure of Giles, A. R. et al., Blood 60, 727-730 (1982).

Figure 3:
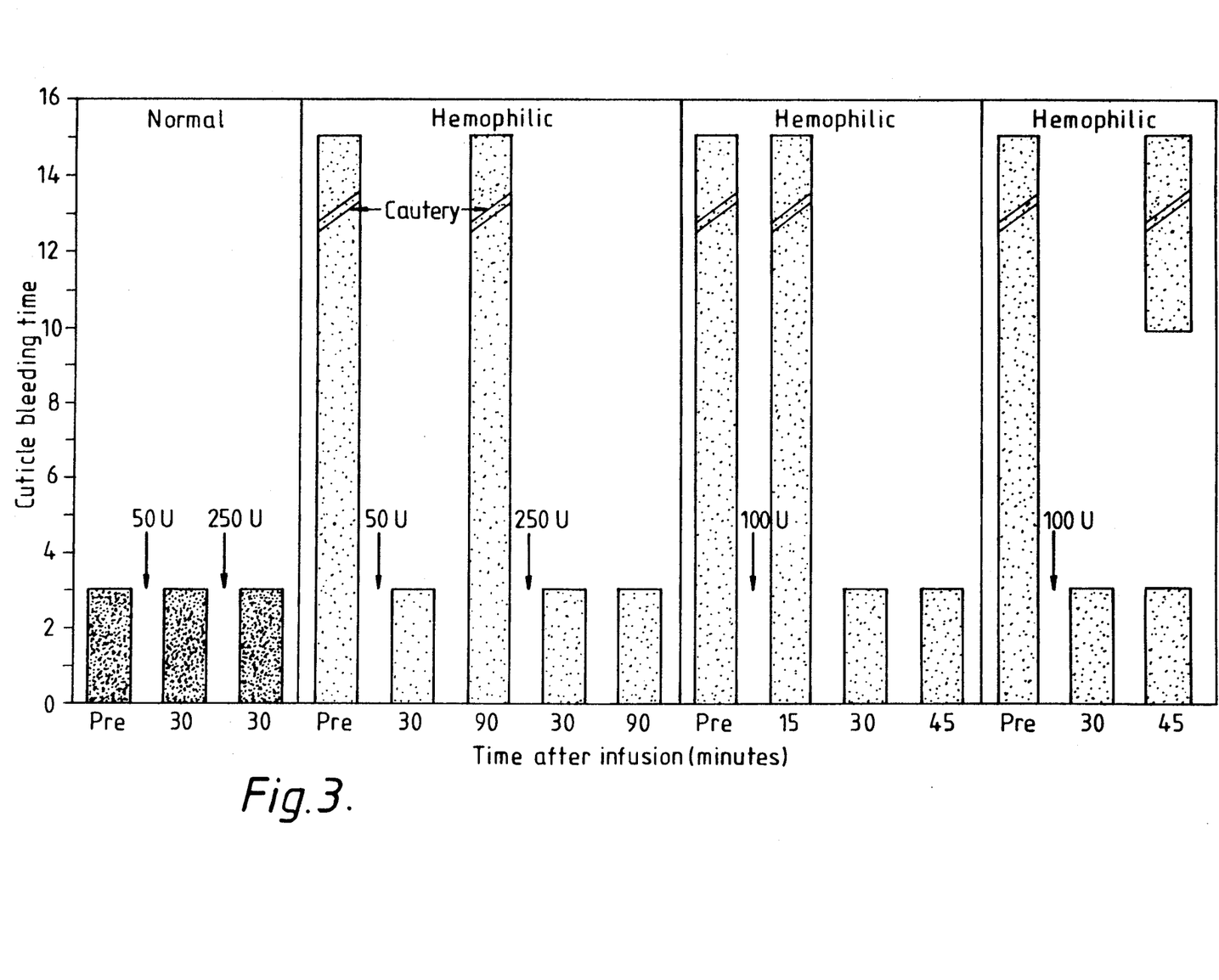
FIG. 3. Cuticle bleeding times (CBT) in animals receiving tissue factor protein Arrows denote dose of tissue factor protein in U/kg. Pre refers to CBT prior to any injection.

Lack of tissue factor protein toxicity was first determined in a normal dog on bolus injection of 50 tissue factor protein U/kg and 250 tissue factor protein U/kg doses. A cuticle bleeding time (CBT) was performed (Giles suora) prior to infusion and 30 min after each injection. Blood was withdrawn and anticoagulated for coagulation assays at various time points during the experiment (FIG. 3). In order to demonstrate in vivo factor VIII bypassing activity of tissue factor protein, experiments were conducted using hemophilic dogs. Fasting animals were anesthetized and a CBT performed prior to any infusion. Tissue factor protein was then administered by bolus injection and CBTs performed at various time points up to 90 min after the infusion. Several doses of tissue factor protein were administered. Blood samples were withdrawn throughout the duration of each experiment and assayed for factor V, prothrombin and partial thromboplastin times. CBTs of greater than 12 min were regarded as grossly abnormal. Those nails were cauterized to prevent excessive blood loss.

An anesthetized normal dog was administered doses of tissue factor protein representing 50 and 250 U/kg of tissue factor protein on relipidation in the chromogenic assay. The CBT in this animal was approximately 3 min prior to any infusion (FIG. 3) Factor V levels were normal 30 min after each infusion (Table 6). The prothrombin and partial thromboplastin times were unchanged at the end of the experiment and the CBTs were also within the normal range. Thus the infusion of tissue factor protein was well tolerated in normal dogs and no evidence of disseminated intravascular coagulation was found.

A hemophilic dog with a prolonged CBT characteristic of hemophilia A was administered 50 U/kg of tissue factor protein. The CBT was normalized 30 min after this infusion (FIG. 3). This correction was not associated with an alteration in factor V levels, nor was the prothrombin time lengthened (Table 6). The procoagulant effect was not maintained 90 min after the infusion as the CBT effect was again abnormal at this time point. A dose response relationship was established by infusion of 250 tissue factor protein U/kg. At this dose, the CBT of the hemophilic dog was normalized at 30 and 90 min (FIG. 3). This increased dosage was, however, associated with a decrease in factor V levels and a slight lengthening of the prothrombin time (Table 6). As a consequence, experiments were repeated using a dose of 100 tissue factor protein U/kg in order to obtain the maximum duration of efficacy while ensuring that other coagulation factor levels were unaffected. Thus, a hemophilic dog received 100 tissue factor protein U/kg and CBT performed at 15, 30 and 45 min. Interestingly, the CBT at 15 min was still abnormal (FIG. 3) and stasis was not achieved until 30 min after the infusion. This is an observation consistent with results obtained using conventional canine factor VIII preparations in non-inhibitor hemophilic dogs. At this dose, the CBT was normal at 45 min. Blood samples were taken and analyzed for evidence of consumptive coagulopathy (Table 6). Factor V levels, prothrombin times, thrombin clotting times and platelet levels were unchanged by the treatment. Thus, the efficacy of tissue factor protein in vivo was demonstrated at a dose which did not cause disseminated intravascular coagulation. The bypassing activity was confirmed in a third hemophilic dog using a dose of 100 tissue factor protein U/kg and CBTs performed at 30 and 45 min. While efficacy was established at both time points, some rebleeding occurred at 45 min.

EXAMPLE 4

Functional Homology Between Bovine and Human Tissue Factor Proteins

Functional homology between bovine and human tissue factor proteins was shown using the chromogenic tissue factor assay. Bovine tissue factor protein was purified as described above Human tissue factor protein was partially purified from placentae using the method of Freyssinet et al, Thrombosis and Haemostasis 55(1):112-118 (1986) including affinity chromatography on Concanavalin-A Sepharose. The eluted material from this column was then subjected to gel filtration chromatography on an AcA 44 Ultrogel column as described earlier for the bovine protein.

Bovine and human tissue factor proteins (referred to as BTFP and HTFP respectively in Table 5) were assayed in the standard chromogenic tissue factor assay already described. Samples that had been relipidated prior to assay exhibited potent tissue factor cofactor activity (referred to as BTFP+P1 and HTFP+P1 respectively in Table 5). Samples that had not been relipidated did not show cofactor activity in the assay (BTFP−P1 and HTFP−P1).

Protein concentrations in these samples were bovine tissue factor protein 0.59 mg/ml and human tissue factor protein 13.55 mg/ml. The difference in protein concentration was a result of differences in the degree of purification. These results are evidence of the functional homology between the tissue factor proteins from human and bovine sources.

TABLE 1

Purification of Bovine Brain Tissue Factor

| Sample | Vol. ml. | Protein mg/ml | Protein Total | Tissue Factor Activity U/ml | Tissue Factor Activity Total | Sp. Acct. U/mg | Purification Fold |
|---|---|---|---|---|---|---|---|
| Acetone Brain Powders | 3,500 | 7.35 | 25,725 | 1.06 | 3,675 | 0.14 | — |
| TBS Wash Supernatant | 3,000 | 6.04 | 18,120 | 0.16 | 480 | — | — |
| 0.1% Triton Supernatant | 3,000 | 1.42 | 4,260 | 0.52 | 1,560 | — | — |
| 2% Triton Extract | 2,750 | 3.00 | 8,250 | 14.82 | 40,761 | 4.94 | 35.2 |
| Con A Sepharose Supernatant | 2,750 | 2.4 | 6,600 | 4.2 | 1,133 | — | — |
| Con A Sepharose Eluate | 420 | 0.2 | 71.4 | 53.5 | 22,470 | 314.0 | 2,242 |
| Con A Eluate Post Concentration | 15 | 1.5 | 23 | 750.0 | 11,250 | 489.0 | 3,492 |
| Ultrogel AcA 44 Pool | 8 | 0.83 | 6.3 | 1,400 | 10,780 | 1,711.0 | 12,221 |

TABLE 2

Characterization of Partially Purified Tissue Factor Protein

| Sample | Chromogenic Assay U/ml | Clotting Time Secs. |
|---|---|---|
| TBS/0.1% Triton buffer | 0 | 250 |
| Tissue Factor Protein | 0 | 249 |
| Relipidated TF | 1,400 | 66.2 |

TABLE 3

Results of in vitro Tissue Factor Protein Bleeding Correction

| No. | Rabbit | Infusion | Factor VIII U/ml Pre | Factor VIII U/ml 30 min. | Factor VIII U/ml 60 min. | Bleeding Time (min) | Bleeding Vol. |
|---|---|---|---|---|---|---|---|
| 1. | Control | TBS/TX100 | 5.0 | 0 | 0 | 11.0 | 15.2 |
| 2. | Test | TFP 233 U/kg* | 4.8 | 0 | 0 | 0.63 | 0.125 |

*233 U/kg of tissue factor activity after relipidation as measured in the chromogenic assay.

TABLE 4

Survival after infusion of Tissue Factor Protein

| No. (+/−) | Wt (kg) | Time 0 Infusion of TFP* Total U | Time 0 Infusion of TFP* U/kg | 72 Hours Infusion of TFP* Total U | 72 Hours Infusion of TFP* U/kg | 120 Hours Survival |
|---|---|---|---|---|---|---|
| 1 | 1.42 | 350 | 246 | 350 | 246 | + |
| 2 | 1.35 | 350 | 260 | 350 | 260 | + |
| 3 | 1.40 | 350 | 250 | 700 | 500 | + |
| 4 | 1.33 | 350 | 263 | 1,750 | 1,316 | + |
| 5 | 1.41 | 350 | 248 | 0 | 0 | + |
| 6 | 1.23 | 350 | 285 | 0 | 0 | + |

*Units were determined by chromogenic assay after relipidation of tissue factor protein samples.

TABLE 5

Functional Homology between Bovine and Human Tissue Factor

| Sample | Assay Dilution | Absorbance 405 nm | Tissue Factor Activity U/ml |
|---|---|---|---|
| BTFP + Pl | 500 | 0.785 | 800 |
| BTFP + Pl | 1000 | 0.395 | 755 |
| BTFP − Pl | 10 | 0.000 | 0 |
| HTFP + Pl | 500 | 0.892 | 950 |
| HTFP + Pl | 1000 | 0.491 | 910 |
| HTFP − Pl | 10 | 0.000 | 0 |

TABLE 6

Blood Parameters in Normal and Hemophilic Dogs Following Bolus Injection of Tissue Factor Protein

| Dog | Dose Tissue Factor Protein (U/kg) | Sample Time Post Infusion (min) | PT (sec) | PTT (sec) | Factor V (U/ml) | Platelets (10⁶/ml) |
|---|---|---|---|---|---|---|
| N | 50 | PRE | 12 | 21 | 0.81 | ND |
|   |   | 67 | 12 | 22 | 0.96 | ND |
|   | 250 | 30 | 12 | 19 | 1.07 | ND |
|   |   | 60 | 12 | 16 | 1.22 | ND |
| H1 | 50 | PRE | 13 | 53 | 1.01 | ND |
|   |   | 150 | 13 | 54 | 1.03 | ND |
|   | 250 | 32 | 15 | 71 | 0.64 | ND |
| H2 | 100 | PRE | 13 | 51 | 1.24 | 205 |
|   |   | 15 | 13 | 51 | 1.23 | 169 |
|   |   | 57 | 13 | 51 | 1.17 | 223 |

Coagulation assay results after bolus injection of tissue factor protein in normal and hemophilic dogs.
N = normal dog
H1 and H2 = hemophilic dogs
ND = not determined.

We claim:

1. A method of treating an animal with a bleeding disorder selected from the group consisting of congenital coagulation disorders, acquired coagulation disorders, and trauma induced hemorrhagic conditions, comprising administering a therapeutically effective dose of a sterile tissue factor protein composition isotonic to blood, substantially devoid of the naturally occurring lipid of tissue factor and possessing substantially no procoagulant activity prior to administration, to an animal having such a bleeding disorder.

2. The method of claim 1 wherein the bleeding disorder is an acquired coagulation disorder.

3. The method of claim 1 wherein the tissue factor protein is administered intravenously or orally.

4. The method of claim wherein the congenital coagulation disorder is a deficiency of a blood factor selected from, the group consisting factor VIII, factor IX, factor XI and factor XIII.

5. The method of claim 1 wherein the therapeutically effective dose is in the range of about from 50 U/kg to 250 U/kg.

6. The method of claim 1 wherein the therapeutically effective dose is in the range of about from 75 U/kg to 200 U/kg.

7. A sterile therapeutic composition is tonic to blood for administration to an animal with a bleeding disorder selected from the group consisting of congenital coagulation disorders, acquired coagulation disorders, and trauma induced hemorrhagic conditions, comprising a therapeutically effective does of human tissue factor protein, substantially devoid of the naturally occurring lipid of tissue factor and possessing substantially no procoagulant activity prior to administration, and a pharmaceutically acceptable vehicle characterized by conferring substantially no procoagulant activity on the tissue factor protein prior to administration.

8. The therapeutic composition of claim 7 wherein the vehicle is a lipophilic sustained release formulation substantially devoid of the naturally occurring lipid of tissue factor.

9. The therapeutic composition of claim 7 wherein the vehicle contains a detergent.

10. The therapeutic composition of claim 9 wherein the detergent is a nonionic detergent.

11. A sterile therapeutic composition isotonic to blood for administration to an animal with a bleeding characterized by a tendency to hemorrhage comprising a therapeutically effective dose of human tissue factor protein substantially devoid of the naturally occurring lipid of tissue factor and possessing substantially no procoagulant activity prior to administration, and a pharmaceutically acceptable vehicle characterized by conferring substantially no procoagulant activity on the tissue factor protein prior to administration in combination with a container having a sterile access port.

12. The method of claim 1 wherein the therapeutically effective dose is in the range of about from 10 U/Kg to 300 U/Kg.

13. The therapeutic composition of claim 8 wherein the lipophilic sustained formulation comprises mineral oil, triglyceride, esterified glycol, polyglycols with alkyl side chains, or sterol.

14. The therapeutic composition of claim 13 wherein the formulation comprises sterol or triglyceride.

15. The therapeutic composition of claim 8 wherein the lipophilic sustained release formulation comprises a liposome.

* * * * *